(12) United States Patent
Adiletta

(10) Patent No.: US 6,672,135 B2
(45) Date of Patent: Jan. 6, 2004

(54) FILTER FOR GAS ANALYSIS

(75) Inventor: Joseph G. Adiletta, Thompson, CT (US)

(73) Assignee: Pall Corporation, East Hills, NY (US)

(*) Notice: Subject to any disclaimer, the term of this patent is extended or adjusted under 35 U.S.C. 154(b) by 0 days.

(21) Appl. No.: 10/181,060

(22) PCT Filed: Jan. 12, 2001

(86) PCT No.: PCT/US01/00879

§ 371 (c)(1),
(2), (4) Date: Oct. 15, 2002

(87) PCT Pub. No.: WO01/51177

PCT Pub. Date: Jul. 19, 2001

(65) Prior Publication Data

US 2003/0192363 A1 Oct. 16, 2003

Related U.S. Application Data

(60) Provisional application No. 60/176,023, filed on Jan. 14, 2000.

(51) Int. Cl.[7] .................. B01D 46/54; B01D 61/00; G01N 1/04; G01N 33/49; G01N 33/493
(52) U.S. Cl. .................. 73/28.04; 73/863.23; 73/28.01; 210/651; 210/321.84; 422/88
(58) Field of Search .............. 73/28.04, 28.01, 73/23.2, 863.23, 864.71; 422/88; 210/651, 321.75, 321.84

(56) References Cited

U.S. PATENT DOCUMENTS

| 2,675,697 A | * | 4/1954 | Quynn et al. ............... 73/28.01 |
| 3,677,065 A | * | 7/1972 | Davis ......................... 73/28.01 |
| 3,814,522 A | * | 6/1974 | Clark et al. .................. 356/197 |
| 3,949,594 A | * | 4/1976 | Treaftis et al. .............. 73/28.01 |
| 4,360,364 A | | 11/1982 | Kohl ............................. 55/96 |
| 4,488,961 A | | 12/1984 | Spencer ..................... 210/136 |
| 4,544,386 A | * | 10/1985 | Trayford, III et al. ........ 55/270 |
| 4,618,533 A | | 10/1986 | Steuck ..................... 428/315.7 |
| 4,715,960 A | | 12/1987 | Thompson ................. 210/651 |
| 4,872,988 A | | 10/1989 | Culkin ....................... 210/636 |

(List continued on next page.)

FOREIGN PATENT DOCUMENTS

| EP | 452 592 | 10/1991 |
| WO | WO 96/14563 | 5/1996 |

OTHER PUBLICATIONS

Pall Gelman Sciences, "Air Sampling Methods Cross–Reference Guide", 6 pages, (© Aug. 1997).
"Introduction to NMAM", (1 page, Internet, Dec. 23, 1999).
"Protocols for Method Evaluation", (1 page, Internet, Dec. 23, 1999).
"Second Supplemental to NIOSH Manual of Analytical Methods", 3rd Ed., (Aug. 15, 1987), (9 pages, including p. V–Xi).
"Nuclepore Filters", Gas Filtration Theory, pp. 146–149.
Marple, Virgil et al.; "Aerosols In the Mining and Industrial Work Environments", vol. 3, pp. 992–993.
Federal Register, vol. 62, No. 138, Rules and Regulations, pp. 38763–38764, (Jul. 18, 1997).
Federal Register, vol. 62, No. 138, Rules and Regulations, p. 38651–38652, (Jul. 18, 1997).
"Other Applications", Gelman Product Guide, p. 4.

*Primary Examiner*—Hezron Williams
*Assistant Examiner*—David J. Wiggins
(74) *Attorney, Agent, or Firm*—Leydig, Voit & Mayer, Ltd.

(57) ABSTRACT

A filter (20) suitable for gas analysis, especially non-gravimetric gas analysis, by collecting particulate matter thereon, with a filter material comprising a polycarbonate membrane having a maximum pore size of 2 micrometers or less that is secured by a support (5) formed of a polyolefin or polymethylpentene material. For additional embodiments, the particular manner of support mounting to the membrane may include thermal-bonding techniques, and the particular method of analysis may include X-Ray luminescence.

23 Claims, 3 Drawing Sheets

U.S. PATENT DOCUMENTS

| | | | |
|---|---|---|---|
| 4,941,742 A | * 7/1990 | Schrader et al. | 356/38 |
| 4,961,916 A | 10/1990 | Lesage et al. | 422/88 |
| 5,042,502 A | * 8/1991 | Guirguis | 128/771 |
| 5,147,553 A | 9/1992 | Waite | 210/654 |
| 5,256,288 A | 10/1993 | Lee | 210/321.61 |
| 5,376,800 A | 12/1994 | Solares et al. | 250/472.1 |
| 5,401,468 A | * 3/1995 | Patashnick et al. | 422/80 |
| 5,445,746 A | 8/1995 | Lee | 210/783 |
| 5,449,917 A | 9/1995 | Clements | 250/492.3 |
| 5,458,719 A | 10/1995 | Pall et al. | 156/285 |
| 5,556,528 A | 9/1996 | Bohn et al. | 204/600 |
| 5,587,070 A | 12/1996 | Pall et al. | 210/202 |
| 5,750,329 A | 5/1998 | Quinn et al. | 435/1.1 |
| 5,804,048 A | 9/1998 | Wong et al. | 204/403 |
| 5,833,927 A | 11/1998 | Raybuck et al. | 422/101 |
| 5,834,633 A | * 11/1998 | Davison | 73/53.01 |
| 5,904,846 A | 5/1999 | Clements et al. | 210/321.77 |
| 5,932,795 A | 8/1999 | Koutrakis et al. | 73/28.01 |
| 5,964,984 A | 10/1999 | Holmbom et al. | 162/49 |
| 5,989,698 A | 11/1999 | Mrozinski et al. | 428/315.7 |
| 6,012,325 A | * 1/2000 | Ma | 73/24.02 |
| 6,057,165 A | 5/2000 | Mansour | 436/518 |
| 6,154,991 A | 12/2000 | Duncan et al. | 38/102.2 |

* cited by examiner

FILTER FOR GAS ANALYSIS

This application claims the benefit of U.S. provisional patent application No. 60/176,023, filed Jan. 14, 2000, which is incorporated by reference.

TECHNICAL FIELD

This invention relates to filters for analyzing gas such as air, and more particularly relates to filters for monitoring particulate matter in ambient air, e.g., in accordance with the Environmental Protection Agency's national ambient air quality standards.

BACKGROUND OF THE INVENTION

There are a variety of protocols and systems for sampling gases such as air. For example, there are National Institute for Occupational Safety and Health (NIOSH) air sampling protocols, as well as methods for surveying ambient air quality in accordance with requirements established by the Environmental Protection Agency (EPA). Illustratively, as set forth in 40 C.F.R §§ 50.1–50.12 with appendices A–N, the EPA has established standards for measuring inhalable particulate matter (PM), referred to as the "$PM_{10}$" standard (for measuring particulate matter with an aerodynamic diameter of less than or equal to a nominal 10 micrometers) and the "$PM_{2.5}$" standard (for measuring particulate matter with an aerodynamic diameter of less than or equal to a nominal 2.5 micrometers). These EPA standards require drawing air through a filter, collecting the suspended particulate matter on the filter over a sampling period, and determining the particulate matter gravimetrically. The collected particles, usually on polytetrafluoroethylene (PTFE) filters, are weighed using microbalances under constant specified temperature and relative humidity conditions.

For example, the EPA $PM_{2.5}$ standard requires drawing ambient air at a constant volumetric flow rate through an inertial particle size separator (impactor) where the suspended particulate matter is separated for collection on a PTFE filter over the specified sampling period. The mass concentration of the particles is computed and expressed in micrograms per cubic meter of air ($\mu g/m^3$).

However, in accordance with the present invention, it has been discovered that some material of interest was not measured when the above-referenced protocols were carried out, e.g., the conventional gravimetric systems lacked the capability and/or sensitivity to collect some of the particles in the gas.

The present invention provides for ameliorating at least some of the disadvantages of the prior art. These and other advantages of the present invention will be apparent from the description as set forth below.

SUMMARY OF THE INVENTION

In accordance with the instant invention, a filter for analyzing gas (e.g., ambient air or chemically contaminated air) is provided comprising a supported porous polycarbonate membrane, wherein the support is secured, e.g., thermally bound, to the polycarbonate membrane. Preferably, the filter has a pore size of about 1 micrometer ($\mu m$) or less, more preferably, about 0.5 micrometers or less.

Filters according to embodiments of the instant invention are suitable for a variety of gas analyzing and/or sampling protocols, including EPA and NIOSH protocols. In preferred embodiments, the filters are suitable for non-gravimetric analysis and sampling protocols, especially for monitoring submicron particulate matter in gas.

In more preferred embodiments, the filter comprises a porous polycarbonate membrane having an annular support secured to the periphery of the membrane, and this configuration allows the filter to be handled easily, while providing a firm gasketing (e.g., sealing) area when the filter is placed in a filter device such as a filter holder, a particle size separator (e.g., an impactor), and/or a filter cassette.

SPECIFIC DESCRIPTION OF THE INVENTION

Each of the components of the invention will now be described in more detail below, wherein like components have like reference numbers.

Figure 1A:
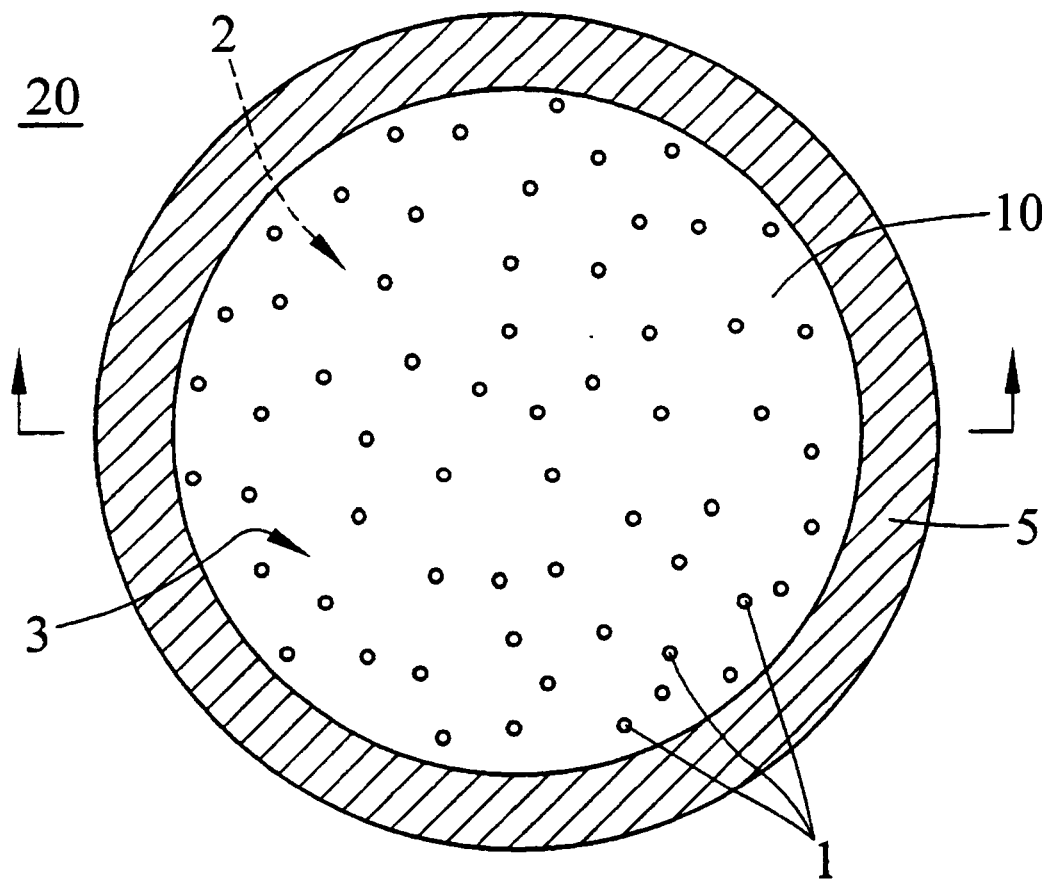
FIGS. 1A and 1B are, respectively, bottom and cross-sectional views of an embodiment of the present invention, showing a filter comprising a porous polycarbonate membrane secured to an annular support.

Using the embodiment illustrated in FIG. 1A (bottom view) and 1B (cross-sectional view) for reference, a filter 20 comprises a porous polycarbonate membrane 10 (having a plurality of pores 1, a first surface 2, and a second surface 3) and a support 5 secured to the second surface of the membrane.

Preferably, the porous polycarbonate membrane comprises (and can consist of, or consist essentially of) a thin-film track-etched polycarbonate sheet. Such polycarbonate membranes are desirable as they provide a more uniform range of pore sizes. These membranes are typically prepared by a process that includes exposing the film to bombardment with particles (e.g., radiation bombardment with heavy ions) to form weakened tracks in the membrane, and the process may include subsequently etching the damaged film with a gas or liquid to form pores. Typically, the prepared membranes have "straight through" pores.

The membrane has a pore structure suitable for collecting the particles of interest. Typically, the membrane has a pore size of about 2.0 micrometers or less, preferably about 1.0 micrometer or less, even more preferably, about 0.5 micrometers or less, e.g., wherein the pore size is measured by bubble point, for example, by ASTM F 316-94 Standard Test Methods for Pore Size Characteristics of Membrane Filters by Bubble Point and Mean Flow Pore Test, or ASTM E 1294-89 (1999) Standard Test Method for Pore Size Characteristics of Membrane Filters Using Automated Liquid Porosimeter. Alternatively, the membrane can be characterized by, for example, aerosol filtration efficiency, e.g., wherein the membrane functions as about a 0.1 micrometer filter or less, preferably about a 0.05 micrometer filter or less, when filtering an aerosol. Another example of characterizing the filter is measuring the membrane efficiency by the Monodisperse DOP (Dioctyl Phthalate) Smoke Test (e.g., ASTM D 2986-95a). For example, the filter can remove particles having a size of 0.2 micrometers or larger with an efficiency of at least 99.9 percent.

The membrane can have a variety of shapes (e.g., circular, oval. square, rectangular, or triangular). Preferably, for ease of handling and subsequent particle analysis, the membrane has a substantially planar configuration.

Typically, the membrane has a thickness in the range of from about 0.1 to about 5.0 mils (about 2.54 to about 127 micrometers), preferably about 0.2 to about 2.0 mils (about 5.08 to about 50.8 micrometers), more preferably, about 0.3 mils to about 1.0 mils (about 7.62 to about 25.4 micrometers).

For some EPA protocols, the membrane has a thickness in the range of about 1.18 mils to about 1.97 mils (about 30 to about 50 micrometers).

Suitable track-etched membranes include commercially available membranes, such as those available under the trade name NUCLEPORE®, and membranes sold by Poretics Corporation (Livermore, Calif.).

The support 5 may comprise (and can consist of, or consist essentially of) any suitable material, such as a metal (e.g., a foil). Preferably, the support comprises a polymeric material, more preferably a substantially inert material such as a polyolefin. Examples of suitable polyolefins include at least one of polypropylene, polyethylene, and polymethylpentene (PMP). In some embodiments, the support comprises a polymeric composite, for example, a polyolefin composite including a polyester.

In a preferred embodiment, the support 5 is secured (e.g., bound) to one side of the membrane 10 without using a separate adhesive. For example, in one embodiment, the support is thermally bound to the membrane, e.g., to provide an integral support. Other suitable techniques for securing the support to the membrane include, for example, at least one of crimping, mechanical stamping, using thermoplastic fibers, using a pressure sensitive tape, and using an adhesive coating. The support can be secured to either side of the membrane, e.g., the "upstream" side (the side first contacted by the gas) or the "downstream" side (the side opposite to the side first contacted by the gas).

As with the membrane 10, the support 5 (and the filter 20) can have a variety of shapes (e.g., round, oval, square, rectangular, or triangular) and preferably has a substantially planar configuration. In a preferred embodiment, the support is in the form of an annular ring.

Figure 1B:
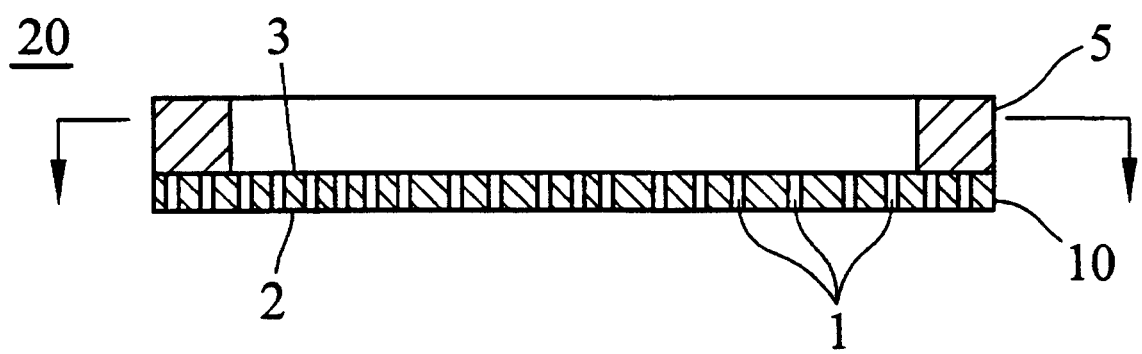

Preferably, the support is arranged to minimize the potential for interference with and/or interruption of flow through the membrane. For example, in a more preferred embodiment, e.g., using the embodiment of filter 20 illustrated in FIGS. 1A and 1B for reference, most of the surface area of the first surface 2 and the second surface 3 of the membrane 10 are non-occluded by the support 5.

Typically, the support (e.g., in the form of an annular ring) is arranged to contact one side of the membrane near or at the periphery of the membrane. In some embodiments (not shown), the support can also contact the other side of the membrane, or an additional support (e.g., an additional annular ring) can be utilized. For example, a first annular ring can be secured to one side of the membrane, and a second support can be placed in secured or unsecured (e.g., unbound) contact with the other side of the membrane. In another example, a first annular ring and a second annular ring having a smaller outer diameter than that of the first annular ring can be applied to opposite sides of the membrane and pressed together such that the membrane is sealed between the first annular ring and the second annular ring, preferably wherein the outer diameter of the second annular ring is less than the inner diameter of the first annular ring.

In some preferred embodiments, e.g., for use in accordance with some EPA, NIOSH, and/or OSHA protocols, including non-gravimetric and gravimetric protocols, the filter comprises a circular membrane disc, with a support ring bound to the periphery of one surface of the membrane.

Illustratively, filters for use in typical EPA and/or NIOSH protocols are about 25 mm, about 37 mm, about 47 mm, about 70 mm, or about 90 mm in diameter.

In those embodiments wherein the support comprises an annular support such as a support ring, the ring has any suitable outside diameter, preferably one that is identical to, or essentially corresponds to, the diameter of the membrane, e.g., about 25 mm, about 37 mm, about 47 mm, about 70 mm, or about 90 mm.

The inside diameter of the support ring can be any suitable diameter. In some typical embodiments wherein the outside diameter of the membrane and the support ring is about 47 mm or less, the inside diameter of the support ring is about 10 mm less than the outside diameter. For example, in an embodiment, the support ring has an outside diameter of about 37 mm and an inside diameter of about 27 mm.

In some typical embodiments wherein the outside diameter of the membrane and the support ring is greater than 47 mm, the inside diameter of the support ring is about 15 mm less than the outside diameter. For example, in an embodiment, the support ring has an outside diameter of about 70 mm and an inside diameter of about 55 mm.

Typically, the support has a thickness of at least about 4.0 mils (about 101.6 micrometers), e.g., in the range from about 6.0 mils to about 20 mils (about 152.4 micrometers to about 508.0 micrometers), preferably in the range of from about 10.0 to about 18.0 mils (about 254.0 micrometers to about 457.2 micrometers).

As noted above, filters according to embodiments of the invention can be used in a variety of gas (especially ambient air or gas emissions) analysis protocols, including NIOSH (e.g., as described in the NIOSH Manual of Analytical Methods (NMAM®) 4th ed. DHHS (NIOSH) Publication 94-113 (August, 1994) Cassinelli, M. E. et al. ed.; as well as described in NMAM® 3rd ed., e.g., as set forth in the Aug. 15, 1987 Supplement to the 3rd ed.), OSHA, ASTM, ISO, and EPA sampling procedures.

The filters can be used for analyzing indoor and outdoor gas, and can be used in gravimetric and non-gravimetric analysis. Preferably, filters according to embodiments of the invention are utilized in non-gravimetric (e.g., at least one of chemical testing, Atomic Absorption, X-Ray Luminescence, and/or X-Ray Powder Diffraction) analytical protocols.

Typically, the filter is disposed in a device that allows gas to flow through the filter from one surface to the other surface, such as at least one of a filter housing, filter holder, filter cassette, and/or an impactor. For example, the device can comprise a housing having an inlet and an outlet and defining a gas flow path between the inlet and the outlet, wherein the filter is disposed in the housing across the flow path. This invention is not limited to any particular device or housing. In some embodiments, the filter is placed in a filter holder, and the filter holder (containing the filter) is placed in a filter cassette (such as an air monitoring cassette) or an impactor. Preferably, the filter can be easily removed from the device(s) or housing(s) after use, e.g., the filter holder is re-usable, and the filter is replaceable. A variety of materials are suitable for use as housings, holders, cassettes, or impactors.

Figure 2:
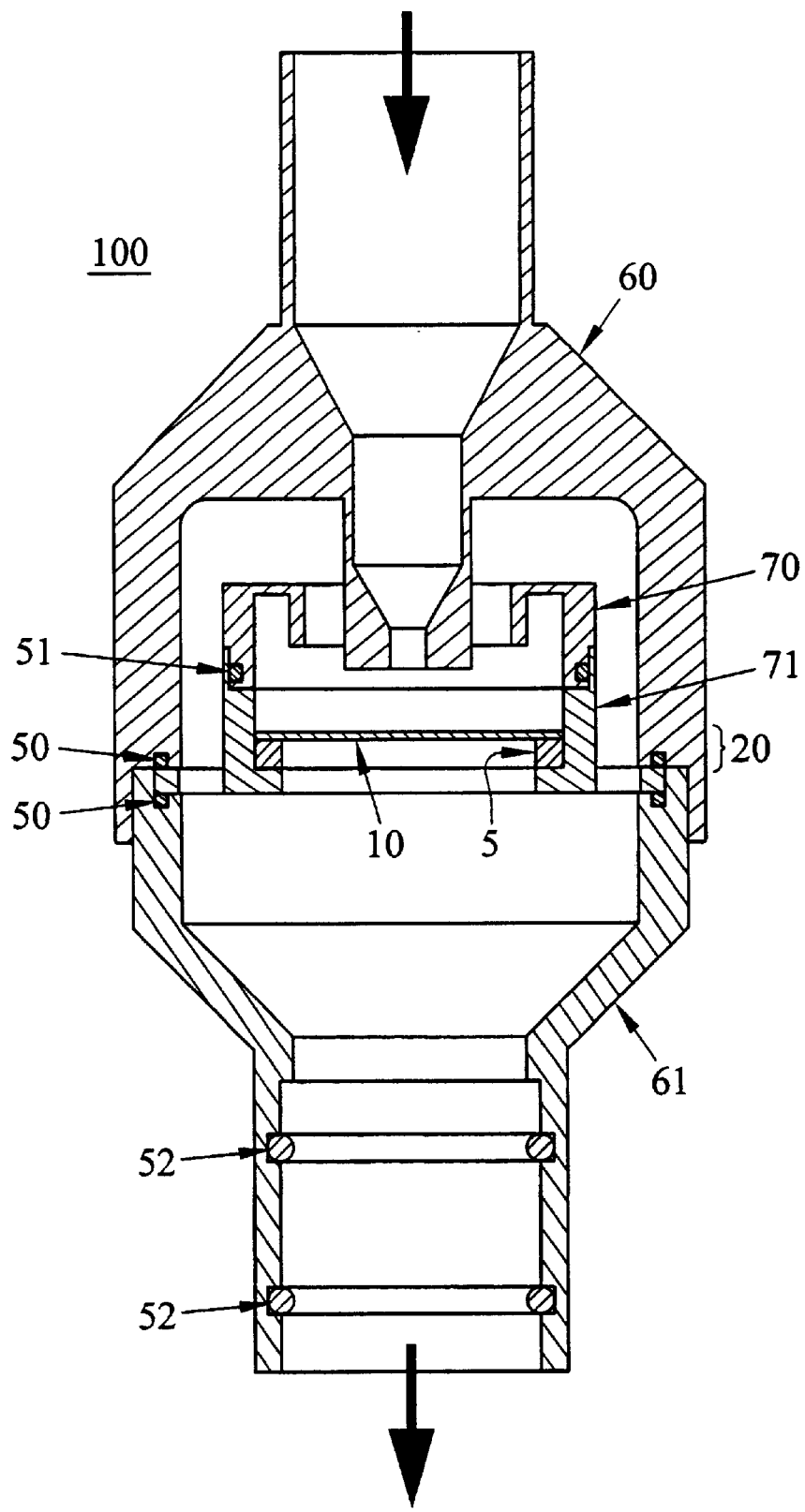
FIG. 2 is a partial cross-sectional view of an embodiment of the present invention, showing an impactor including a filter disposed therein.

One embodiment of a suitable device is illustrated in FIG. 2, showing a partial cross-sectional view of an impactor for use in EPA's $PM_{2.5}$ test as set forth in 40 C.F.R. §§ 50.1–50.12, wherein the filter for the EPA test has been replaced with a filter according to an embodiment of the invention. Accordingly, FIG. 2 shows an impactor 100 having a upper housing 60 and a lower housing 61, an upper impactor well 70 and a lower impactor well 71, a set of two O-rings 50, an O-ring 51, a set of two O-rings 52, and a filter 20 comprising a membrane 10 and a support 5 disposed in the impactor, between the upper and lower housings and the upper and lower impactor wells. In an embodiment (not shown) impactor oil is placed in the impactor before passing gas through the filter.

If desired, the impactor 100 can be utilized in a protocol generally similar to that described in the EPA test.

Figure 3:
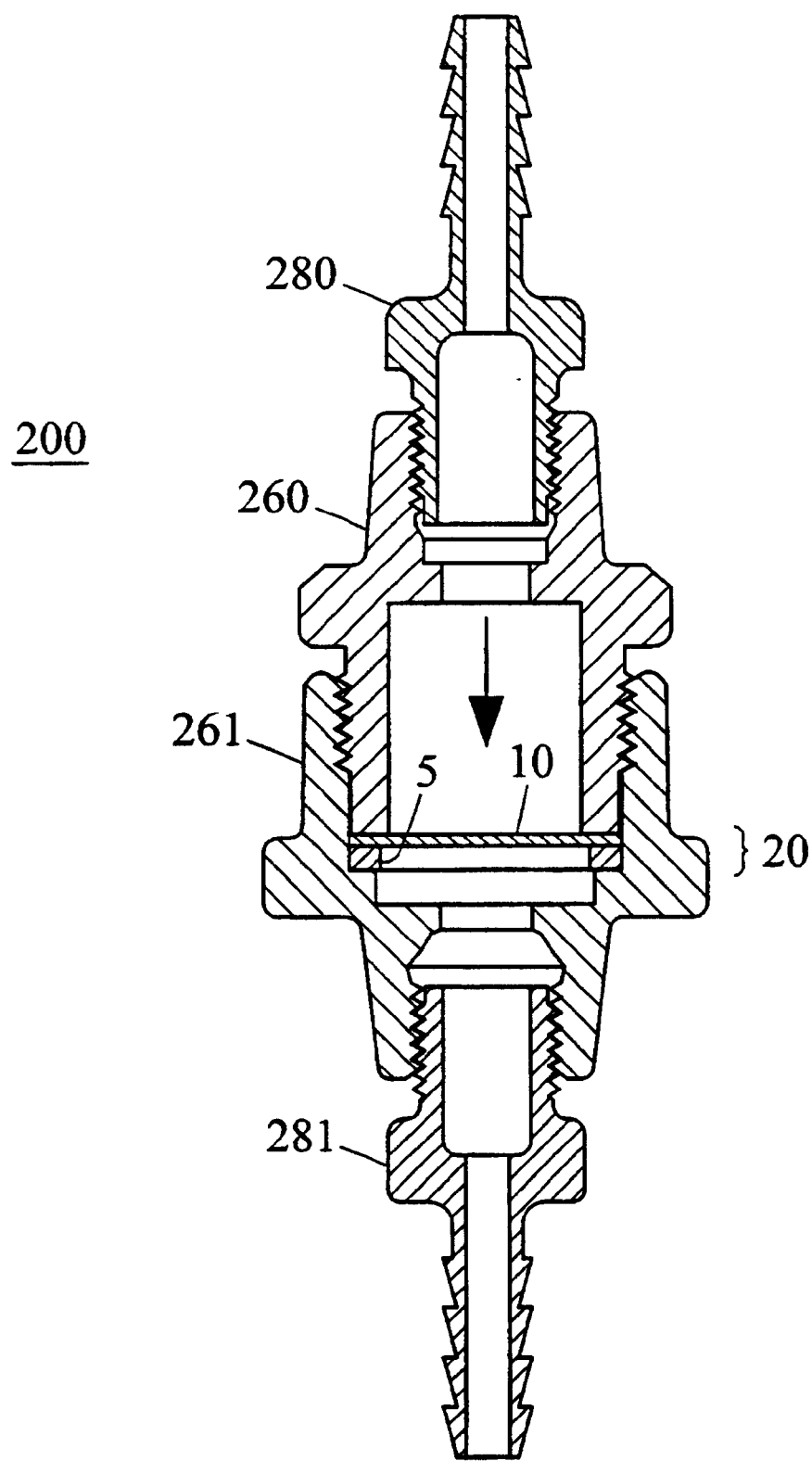
FIG. 3 is a partial cross-sectional view of another embodiment of the present invention, showing a filter holder including a filter disposed therein.

Another embodiment of a suitable device is illustrated in FIG. 3, showing a partial cross sectional view. Accordingly, FIG. 3 shows a filter holder 200 having an upper housing 260 and a lower housing 261, an upper conduit connection port 280 and a lower conduit connection port 281, and a filter 20 comprising a membrane 10 and a support 5 disposed in the filter holder, between the upper and lower housings.

EXAMPLE 1

A NUCLEPORE® polycarbonate membrane having a pore size of 0.4 micrometers ($\mu$m) is obtained, and a 15 mils (about 381 micrometers) thick sheet of polymethylpentene (PMP) is punch-pressed to provide a 37 mm diameter circular hole in the PMP sheet.

The PMP sheet is placed over the polycarbonate membrane, and the two materials are placed in a heat seal chamber for 2 seconds at 400° F. (about 204.4° C.) at 40 p.s.i. (about $2.758 \times 10^5$ Pa) to provide a laminate of thermally bound materials.

The laminate is placed in a punch press including a 47 mm punch-cutting die, and the press is operated to provide a 47 mm outside diameter circular filter, e.g., a membrane with a thermally bonded integral support. The membrane and the support ring each have an outside diameter of 47 mm, and the support ring has an inside diameter of 37 mm.

The filter is placed in a commercially available 47 mm in-line rotatably clampable (threaded) filter holder and the filter holder is clamped, sealing the filter therein.

While an unsupported membrane disc is thin and tends to wrinkle when handled, the filter produced as described above is easy to handle, and the membrane remains flat and taut, e.g., the filter does not fold or bend when it is picked up. The described filter is easily placed accurately in the filter holder, and the filter is not twisted or torque-damaged as the holder is sealed via rotary clamping. The filter is efficiently sealed in the holder, i.e., the seal is leak-free under typical use conditions. Additionally, the location of the support with respect to the membrane minimizes blockage of the membrane, e.g., allowing flow through more of the area of the membrane for particle capture and subsequent analysis. Furthermore, since the membrane remains flat, taut, and undamaged after removal from the holder, the risk of particles being lost during handling of the membrane is reduced. Accordingly, particle analysis can be more accurately carried out.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A filter for analyzing gas by collecting particulate matter onto the filter in a non-gravimetric type analysis comprising:

a polycarbonate membrane having a pore size of about 1 micrometers or less, and a support comprising a polyolefin, the membrane being secured to the support.

2. The filter for analyzing gas according to claim 1, wherein the polycarbonate membrane has a pore size of about 1 micrometer or less.

3. The filter of claim 1, wherein the support comprises polymethylpentene.

4. The filter of claim 1, wherein the support is thermally bonded to the membrane.

5. The filter of claim 1, wherein the support comprises a ring.

6. The filter of claim 1 disposed in a device for analyzing gas, wherein the device comprises a housing having at least one inlet and at least one outlet and defining a gas flow path between the inlet and the outlet, the filter being disposed in the housing across the gas flow path.

7. The filter of claim 1, wherein the support comprises an annular support.

8. A filter for analyzing gas by collecting particulate matter onto the filter in a non-gravimetric type analysis comprising:

a polycarbonate membrane supported by an integral support, wherein the membrane has a pore size of about 2 micrometers or less.

9. The filter of claim 8, wherein the support comprises an annular support.

10. The filter of claim 8, wherein the polycarbonate membrane has a pore size of about 1 micrometer or less.

11. The filter of claim 8, wherein the support comprises polymethylpentene.

12. The filter of claim 8, wherein the support is thermally bonded to the membrane.

13. The filter of claim 8, wherein the support comprises a ring.

14. A method for analyzing gas comprising:

passing gas including particulate matter through a filter comprising a supported polycarbonate membrane having a pore size of about 2 micrometers or less, wherein the membrane is supported by a polyolefin support; and determining the particulate matter collected by the filter.

15. The method of claim 14, wherein the method of analysis comprises X-Ray luminescence.

16. The method of claim 14, including analyzing gas passed from an incinerator.

17. The method of claim 14, wherein determining the particulate matter collected by the filter includes computing the total mass of particulate matter collected divided by the actual volume of air sampled, over a specified sampling period.

18. The method of claim 17 wherein the mass concentration of the particles is computed and expressed in micrograms per cubic unit of air.

19. A non-gravimetric method for analyzing gas comprising:

passing gas including particulate matter through a filter comprising an integrally supported polycarbonate membrane having a pore size of about 1 micrometers or less; and determining the particulate matter collected by the filter.

20. The method of claim 19, wherein the method of analysis comprises X-Ray luminescence.

21. The method of claim 19, including analyzing gas passed from an incinerator.

22. The method of claim 19, wherein determining the particulate matter collected by the filter includes computing the total mass of particulate matter collected divided by the actual volume of air sampled, over a specific sampling period.

23. The method of claim 22, wherein the mass concentration of the particles is computed and expressed in micrograms per cubic unit of air.

* * * * *